United States Patent
Unhoch et al.

(10) Patent No.: US 6,710,017 B2
(45) Date of Patent: Mar. 23, 2004

(54) COMPOSITIONS AND METHODS FOR CONTROLLING ALGAE IN RECIRCULATING WATER SYSTEMS

(75) Inventors: Michael J. Unhoch; Roy D. Vore, both of Wilmington, DE (US)

(73) Assignee: Avecia, Inc., Wilmington, DE (US)

( * ) Notice: Subject to any disclaimer, the term of this patent is extended or adjusted under 35 U.S.C. 154(b) by 0 days.

(21) Appl. No.: 09/777,561

(22) Filed: Feb. 6, 2001

(65) Prior Publication Data

US 2001/0046946 A1 Nov. 29, 2001

Related U.S. Application Data

(60) Provisional application No. 60/180,892, filed on Feb. 7, 2000, and provisional application No. 60/180,893, filed on Feb. 7, 2000.

(51) Int. Cl.[7] .................. A01N 37/20; A01N 43/54; A01N 43/66; A01N 47/18
(52) U.S. Cl. .................. 504/150; 504/154; 504/155; 504/157; 504/158
(58) Field of Search .................. 504/150, 154, 504/155, 157, 158

(56) References Cited

U.S. PATENT DOCUMENTS 5,925,675 A * 7/1999 Uhr et al. .................. 514/508

OTHER PUBLICATIONS

Nilson et al, Antialgal Substances for Iodine–Disinfected Swimming Pools, Applied and Environmental Microbiology, Dec. 1977, pp. 815–822.

Homepage of W.F.ten Berge, pp. 1–3, dated Jan. 31, 2000 http://home.wx5.nl/wwtberge/.

Liping et al: "The effects of three sulfonylurea herbicides and their degradation products on the green *Algaechlorella pyrenoidosa*", CHEMOSPERE, vol. 37, No., 1998, pp. 747–751.

Nystrom et al., "Effects of sulfonylurea herbicides on non-target aquatic micro–organisms." Aquatic Toxicology, vol. 47, No. 1, 1999, pp. 9–22.

* cited by examiner

*Primary Examiner*—S. Mark Clardy
(74) *Attorney, Agent, or Firm*—Law Offices of John A. Parrish

(57) ABSTRACT

The present invention provides compositions and methods for controlling the growth of algae, especially nuisance algae, in recirculating water systems. The water systems encompass industrial and recreational applications. The compounds for use in the compositions and methods of the invention possess anti-algal activity and are selected from a herbicide and an agricultural fungicide or a combination thereof.

45 Claims, No Drawings

COMPOSITIONS AND METHODS FOR CONTROLLING ALGAE IN RECIRCULATING WATER SYSTEMS

The present application is based upon and claims priority from U.S. Provisional patent applications Ser. Nos. 60/180,892 and 60/180,893 filed on Feb. 7, 2000.

FIELD OF INVENTION

The present invention relates to compositions and methods for treating recirculating water systems to inhibit the growth of or kill algae and kits suitable for use in the methods of the present invention.

BACKGROUND OF THE INVENTION

The water in many industrial and recreational recirculating water systems such as cooling towers, swimming pools, spas, ornamental ponds and the like is susceptible to contamination by bacteria, algae, yeast and fungi. These organisms may be pathogens or potential pathogens. Thus, for safety reasons, it is highly desirable to control their growth by the addition of sanitizing agents to the water. It is also desirable for aesthetic reasons, to control the growth of non-pathogenic bacteria, algae, yeast and fungi, particularly the so-called "nuisance" algae, yeast and fungi which cause discoloration and/or staining of the water and surfaces in contact with the water.

A variety of sanitizing agents have been employed for controlling undesirable microorganisms in recreational recirculating water systems. The most common sanitizing agents provide free chlorine and/or bromine (typically at a concentration in the water of 1 to 5 ppm free halogen). Chlorine may be provided either directly as chlorine gas, sodium or calcium hypochlorite or via a chlorine release agent such as a chlorinated isocyanurate or chlorinated hydantoin. Chlorine may also be liberated in situ by electrolysis of sodium chloride. Other sanitizing agents which have been used in such systems include ozone, ozone forming chemicals, hydrogen peroxide, hydrogen peroxide forming chemicals, copper and/or silver salts which provide copper, silver or chelated copper ions (typically at a concentration in the water of 0.1 to 1.0 ppm), quaternary amines and polymeric biguanides, especially poly(hexamethylene biguanide (hereinafter referred to as PHMB) which is typically used at a concentration in recreational water of 6–10 ppm. Systems employing ultraviolet light have also been used to sanitize recirculating water. In industrial recirculating systems, sanitizing agents are used at higher concentrations and other sanitizing agents may be used, including but not limited to, 2-methylisothiazolinone, 5-chloro-2-methylisothiazolinone, benzisothiazolinone, 2-bromo-2-nitropropane-1,3-diol, 1,2-dibromo-2,4-dicyanobutane, methylene bisthiocyanate, 2-(thiocyanomethylthio)-benzothiazole, formaldehyde and formaldehyde release agents, glutaraldehyde, dibromonitrilopropionamide and bromo-hydroxyacetophenone or mixtures thereof.

Although these sanitizing agents are very effective in controlling bacteria, they do not suitably control the growth of the so-called "nuisance" algae, which can cause discoloration and/or staining of the water and surfaces in contact with the water.

Examples of "nuisance" algae which are found in swimming pools include eukaryotic and prokaryotic algae, for example, green algae (e.g. Chlorella spp.), black algae (e.g. Phormidium spp.) and mustard algae (e.g. Eustigmatos spp.). Of these, mustard algae are particularly difficult to control, regardless of the type of sanitizing agent used.

The widespread occurrence of "nuisance" algae has lead to the introduction of methods of controlling these persistent microbes such as dosing with larger amounts of the sanitizer, shock dosing with chlorine or the introduction of further sanitizers or additives such as chelated copper, copper sulfate, combinations of chlorine and ammonium sulfate, colloidal silver, linear and/or cyclic quaternary amine compounds and polyquaternary amine compounds. However, these methods and algaecides have shown only limited efficacy against the "nuisance" algae and can give rise to undesirable levels of foam, especially in re-circulating water systems such as spas. Furthermore, in some circumstances, the additives themselves (especially chelated copper and copper sulphate) can cause staining of surfaces in contact with the water.

Any anti-algal agent to be added to recreational water systems to control "nuisance" algae, must meet a number of demanding performance criteria. These criteria include:

a) an excellent toxicology profile;

b) reasonable solubility;

c) freedom from unpleasant taste d) odorless or free from unpleasant odors;

e) non-staining of construction materials e.g. plaster, plastic;

f) stability to light;

g) stability to other chemicals which may be present in the recirculating water system, for example sanitizers, water clarifiers, oxidizing agents and chelating agents;

h) little or no effect on foaming; and i) no adverse effect on water appearance e.g. discoloration or turbidity.

It has been proposed to add herbicides such as Simazine™ (CAS number 122-34-9, 6-chloro-N2,N4-diethyl-1,3,5-triazine-2,4-diamine) or Erase™ (CAS number 5915413, 1,3,5-triazine-2,4-diamine, 6-chloro-N-(1,1-dimethylethyl)-N'-ethyl-2-tert-butylamino-4-chloro-6-ethylamino-s-triazine) to recreational waters in order to control the "nuisance" algae. However, such chemicals have relatively high mammalian toxicity at the levels required to control the algae, and are thus not suitable in practice for this purpose.

In addition, the following herbicides and agricultural fungicides are not considered within the scope of the invention for controlling the growth of nuisance algae in recirculating water systems:

(i) the herbicide 2-chloro-4,6-diamino-s-triazine of the Formula (1) as disclosed in U.S. Pat. No. 4,659,359 used in combination with active halogen or an agent which releases active halogen;

(ii) the herbicide 4-fluoroalkyl diphenylether as described in U.S. Pat. No. 5,158,596 at col. 3, lines 10 to 40 used in combination with a material selected from the group consisting of sodium hypochlorite, halodialkylhydantoin, n-alkyl dimethyl benzylammonium chloride, 2,2-dibromo-3-nitrilopropionamide, 2-bromo-2-nitro-1,3-propanediol, poly[oxyethylene(dimethylimino)ethylene(dimethylimino) ethylene dichloride], 3-iodo-2-propynylbutylcarbamate, sodium N-methyldithiocarbamate, zinc bis(dimethyldithiocarbamate), p-tolyldiiodomethylsulfone and a fatty acid salt;

(iii) when the herbicide is used in a swimming pool in combination with iodine, the herbicide is not one of those disclosed in Table 1, page 817, of *Applied and Environmental Microbiology*, 1977 Vol. 34, no 6;

(iv) when the herbicide is used in an industrial recirculating water system, it is not a methylthiotriazine derivative of the Formula (1) as described in JP 09 328405 used in combination with 3-(3,4-dichlorophenyl)-1,1-dimethylurea or 3-(3,4-dichlorophenyl)-1-methoxy-1-methylurea;

(v) the herbicide is not Simazine™ (CAS number 122-34-9, 6-chloro-N2,N4-diethyl-1,3,5-triazine-2,4-diamine) or Erase™ (CAS number 5915413, 1,3,5-triazine-2,4-diamine, 6-chloro-N-(1,1-dimethylethyl)-N'-ethyl-2-tert-butylamino-4-chloro-6-ethylamino-s-triazine);

(vi) the agricultural fungicide is not a flavenoid aldehyde or alcohol of the Formula (1) described in U.S. Pat. No. 5,738,861; and (vii) when the agricultural fungicide is used in a swimming pool in combination with iodine, it is not one of those disclosed in Table 1, page 817, Applied and Environmental Microbiology, 1977 Vol. 34, no 6.

None of these have been successful in controlling the growth of nuisance algae in recirculating water systems.

Thus, there is and remains a need for compositions and methods of treating recirculating water systems to control the growth of those "nuisance" algae which persist in the presence of a sanitizing agent.

SUMMARY OF THE INVENTION

According to the present invention, there are provided compositions and methods for inhibiting the growth of or killing algae, particularly nuisance algae, in a recirculating water system comprising adding to the water a compound having anti-algal activity selected from the group of a herbicide or an agricultural fungicide and combinations thereof, said compound having the desired anti-algal activity with respect to the nuisance algae described above.

By way of the present invention, kits containing compounds or compositions for controlling the growth of nuisance algae, as well as other pathogenic organisms in recirculating water systems, are also provided.

The compositions and methods of the present invention are especially suitable for use in recirculating water systems of either an industrial or recreational nature for advantageously controlling the growth of nuisance algae in such recirculating waters.

By the term "anti-algal activity", it shall be understood in the present context to mean that the compound advantageously kills or inhibits the growth of algae, particularly the nuisance algae described above, in recirculating water systems.

DETAILED DESCRIPTION

The compounds having anti-algal activity, particularly with respect to the nuisance algae in recirculating water systems, for use in the present invention are described hereinafter.

Herbicide

The herbicide for use in the present invention is preferably sufficiently water-soluble to provide a concentration of the herbicide in the recirculating water system which is sufficient to inhibit the growth of or kill algae, particularly nuisance algae, present in the recirculating water system. When the herbicide is added to a recreational recirculating water system such as a swimming pool or spa, it is also preferable that it possesses sufficient water-solubility, so as not to adversely affect the appearance of the water in the recirculating water system, for example, by discoloring the water or by causing water turbidity.

Preferably, the herbicide has a water-solubility of at least 1 ppm, more preferably at least 2 ppm, especially at least 5 ppm, more especially at least 50 ppm, and particularly at least 100 ppm. The upper limit of the herbicide's water-solubility does not matter, although typically, the commercially available herbicides have a water-solubility below 100,000 ppm, more usually below 25,000 ppm.

The term "ppm" means parts per million by weight. One may easily determine the water-solubility of a herbicide in ppm because this is the same as the weight of herbicide in milligrams which will dissolve in 1 liter of water at 20° C. For example if 10 mg of herbicide dissolves in 1 liter of water at 20° C., the water-solubility is 10 ppm.

The solubility of many herbicides is influenced by pH. In recirculating water systems, the pH is preferably in the range of from about 6.5 to 9.0, more preferably from about 6.8 to 8.5 and especially from about 7.0 to 8.2. Accordingly, the above-mentioned preferred solubility of the herbicide is the solubility in water at the pH of the recirculating water system.

The herbicide is preferably added to the water system to give a concentration thereof in the range of about 0.1 to 30 ppm, more preferably about 0.1 to 24 ppm, especially about 0.2 to 15 ppm, more especially about 0.5 to 10 ppm.

The herbicide is preferably selected from a group classified by mode of action and chemical family where the modes of action are: inhibition of acetyl CoA carboxylase, inhibition of acetolactate synthase, inhibition of photosythesis at photosystem II, inhibition of protoporphyrinogen oxidase, bleaching, inhibition of microtubule and mitosis organization and cell division, inhibition of cell wall synthesis, and inhibition of lipid synthesis and from the following chemical families: cyclohexanediones, imidazolinones, sufonylureas, triazinones, benzothiadiazinones, uracils, pyridazinones, ureas, amides, diphenylethers, triazolinones, isoxazolidinones, carbamates, chloracetamides, nitriles, thiocarbamates and triazines and mixtures thereof, except for 6-chloro-N2,N4-diethyl-1,3,5-triazine-2,4-diamine and 1,3,5-triazine-2,4-diamine, 6-chloro-N-(1,1-dimethylethyl)-N'-ethyl-2-tert-butylamino-4-chloro-6-ethylamino-s-triazine.

Examples of suitable acetyl CoA carboxylase inhibitors include cyclohexanediones, such as alloxydim, clethodim and sethoxydim.

Examples of suitable acetolactate synthase inhibitors include imidazolinones, such asimazethapyr; and sulfonylureas, such as bensulfuron-methyl, chlorimuron-ethyl, chlorsulfuron, halosulfuron-methyl, metsulfuron-methyl and triflusulfuron-methyl.

Examples of suitable photosystem II photosynthesis inhibitors include triazines such as ametryn and prometryn; triazinones such as hexazinone and metribuzin; benzothiadiazinones such as bentazon; uracils such as terbacil; pyridazinones such as chloridazon; ureas such as chloroxuron and amides such as propanil.

Examples of suitable protoporphyrinogen oxidase inhibitors include diphenylethers such as acifluoren-sodium and triazolinones such as carfentazone-ethyl.

Examples of suitable bleaching herbicides include pyridazinones such as norflurazon and isoxazolidinones such as Clomazone.

Examples of suitable microtubule and mitosis organizatin and cell division inhibitors include carbamates such as asulam, chlorpropham and propham and chloracetamides such as alochlor and metolachlor.

Examples of suitable cell wall synthesis inhibitors include nitriles such as dichlobenil.

In one embodiment, the herbicide is preferably free from triazine groups.

In another embodiment, the herbicide is free from 4-fluoroalkyldiphenylether groups.

The herbicide preferably has a margin of exposure versus no observed effect level ("NOEL") value of greater than 10, more preferably greater than 50, especially greater than 80, and more especially greater than 99. The margin of exposure versus NOEL is determined by estimating the total daily dose of the herbicide to a child in a swimming pool and determining the ratio of the NOEL to this. The total daily exposure may be estimated as follows. Oral exposure is estimated by assuming that the swimmer is in the water 3 hours per day, and that the swimmer ingests 50 milliliters of pool water per hour of swimming. It is also assumed that the herbicide will be present in the pool water at a concentration of 10 parts per million, equivalent to 10 milligrams per liter of pool water. The daily oral exposure is therefore estimated as the product of the swimming duration, the ingestion rate, and the concentration in the pool water. Dermal exposure is estimated by assuming the swimmer is in the water 3 hours per day, that the total body surface area, 8800 square centimeters, is immersed in the water, and that the herbicide permeates the skin at a rate, expressed in centimeters per hour, predicted by a model for skin permeation based on chemical structure, the Skinperm model, developed by W. F. ten Berge. A short description of the Skinperm model, can be accessed at: http://home.wxs.nl/~wtberge/, which is incorporated herein by reference. The daily dermal exposure is then estimated as the product of the permeation rate, the concentration of the herbicide in the pool water (expressed in milligrams per cubic centimeter), the swimming duration, and the total body surface area. The total daily exposure is estimated as the sum of the daily oral and daily dermal exposure. The daily dose, expressed in milligrams per kilogram bodyweight per day, is then estimated as the total daily exposure divided by an assumed body weight of 22 kilograms.

The herbicide preferably has a margin of exposure versus RfD value (Reference Dose, established by the EPA) of less than 1, more preferably less than 0.8, especially less than 0.5, and more especially less than 0.1. The margin of exposure versus RfD is determined by estimating the total daily dose of the herbicide to a child in a swimming pool, as described above, and determining the ratio of the RfD to this (i.e. margin of exposure/RfD).

Preferably, the herbicide is such that when incorporated in the water the presence of the herbicide cannot be detected by the human nose (i.e. it is odorless or has no offensive odor). This is of particular relevance for recreational waters.

Examples of suitable herbicides for use in the present invention and their properties are shown in Table A below:

TABLE A

| Generic Name | Chemical Name | Trade Name | CAS Number | Suppliers | Margin of Exposure vs NOEL (Target > 100) | Margin of Exposure vs. RfD (Target > 1) | Solubility mg/l |
| --- | --- | --- | --- | --- | --- | --- | --- |
| Alachlor | 2-chloro-2',6'-diethyl-N-(methoxymethyl) acetanilide | Partner | 15972-60-8 | Monsanto | 13 | 0.1 | 242 |
| Ametryn | 2-ethylamino-4-isopropylamino-6-methylthio-s-triazine | Evik | 834-12-8 | CIBA | 25 | 0.02 | 185 |
| Bensulfuron ME | Methyl 2-[[[[[(4,6-dimethoxypyrimidin-2-yl)amino]carbonyl]amino]sulfonyl]methyl]-benzoate | Londax | 83055-99-6 | DuPont | 265 | 2.7 | 80–880 |
| Bentazon | 3-isopropyl-1H-2,1,3-benzothiadiazin-4(3H)-one 2,2-dioxide | Basagran | 25057-89-0 | BASF | 41 | 0.4 | 2300 |
| Carfentrazoneethyl | Ethyl a, 2-dichloro-5-[4-(difluoromethyl)-4,5-dihydro-3-methyl-5-oxo-1H-1,2,4-triazol-1-yl]-4-fluorobenzenepropanoate | Shark | 128639-02-1 | FMC | | | 12 |
| Chloridazon | 5-amino-4-chloro-2-phenyl-3(2H)-pyridazinone | Pyramin | 1698-60-8 | BASF | | | 340 |
| Chlorimuron | Ethyl-2-[[[[(4-chloro-6-methoxy-2-pyrimidinyl)amino]-carbonyl]amino]sulfonyl]benzoate | DuPont Classic Herbicide | 90982-32-4 | DuPont | 83 | 0.3 | 1200 |
| Chloroxuron | 3-[p-(p-chlorophenoxy)phenyl]-1,1-dimethylurea | Tenoran | 1982-47-4 | Ciba-Geigy | | | 3.7 |
| Chlopropham | Isopropyl 3-chlorocarbanilate; isopropyl 3-chlorophenylcarbamate | Beet-Kleen | 101-21-3 | Atochem, N. America | 67 | 0.7 | 89 |
| Chlorsulfuron | 2-chloro-N-[[(4-methoxy-6-methyl-1,3,5-triazin-2-yl)amino]carbonyl]benzenesulfonamide | Glean | 64902-72-3 | DuPont | 67 | 0.7 | 300–2800 |
| Clomazone | 2-[(2-chlorophenyl)methyl]-4,4-dimethyl-3-isoxazolidinone | Command | 81777-89-1 | FMC Eastsun Chemical Co., Ltd | 41 | 0.02 | 1100 |
| Dichlobenil | 2,6-diclorobenzonitrile | Casoron | 1194-65-6 | Uniroyal | | | 21 |
| Endothall | 7-oxabicyclo[2,2,1]heptane-2,3-dicarboxylic acid | Aquathol | 145-73-3 | Elf Atochem | 1 | 0.3 | Soluble |
| Halosulfuronmethyl | Methyl 5-{[(4,6-dimethoxy-2-pyrimidinyl)amino]carbonylaminosulfonyl}-3-chloro-1-methyl-1H-pyrazole-4-carboxylate | Battalion | 100784-20-1 | Monsanto | 133 | 1.3 | 15 |

TABLE A-continued

| Generic Name | Chemical Name | Trade Name | CAS Number | Suppliers | Margin of Exposure vs NOEL (Target > 100) | Margin of Exposure vs. RfD (Target > 1) | Solubility mg/l |
|---|---|---|---|---|---|---|---|
| Hexazinone | 3-cyclohexyl-6-(dimethylamino)-1-methyl-1,3,5-triazine-2,4(1H,3H)-dione | Velpar | 51235-04-2 | DuPont | 63 | 0.6 | |
| Imazethapyr | 2-[4,5-dihydro-4-methyl-4-(1-methylethyl)-5-oxo-1H-imidazol-2-yl]-5ethyl-3-pyridinecarboxylic acid | Pursuit | 101917-66-2 | American Cyanamid | 3333 | 3.3 | 1400 |
| Metribuzin | 4-amino-6-(1,1-dimethylethyl)-3-(methylthio)-1,2,4-triazin-5(4H)-one | Lexone | 21087-64-9 | DuPont | 33 | 0.3 | |
| Metsulfuron-methyl | Methyl 2-[[[[(4-methoxy-6-methyl-1,3,5-triazin-2-yl)amino]carbonyl]amino]sulfonyl]benzoate | Ally | 74223-64-6 | DuPont | 333 | 3.3 | 1750–9500 |
| Molinate | S-ethyl hexahydro-1H-azepine-1-carbothioate | Ordram | 2212-67-1 | Zeneca | 3 | 0.03 | 880 |
| Norflurazon | 6-chloro-N-methyl-N'-(1-methylethyl)-1,3,5-triazine-2,4-diamine | Predict | 27314-13-2 | Novartis | 20 | 0.3 | 28 |
| Pebulate | S-Propyl butyl(ethyl)thiocarbamate | Tillam | 1114-71-2 | Zeneca | | | 60 |
| Prometryn | N,N'-bis(1-methylethyl)-6-(methylthio)-1,3,5-triazine-2,4-diamine | Caparol (80W) | 7287-19-6 | Ciba-Geigy | 50 | 0.1 | 33–48 |
| Propanil | N-(3,4-dichlorophenyl)propanamide | Arosol | 709-98-8 | Rohm and Haas | 67 | 0.1 | 225 |
| Propham | 1-methylethylphenyl carbamate | Chem Hoe | 122-42-9 | | | | 250 |
| Sethoxydim | 2-[1-(ethoxyimino)butyl]-5-[2-(ethylthio)propyl]-3-hydroxy-2-cyclohexen-1-one | Poast | 74051-80-2 | BASF | 119 | 12 | 4700 |
| Terbacil | 3-tert-Butyl-5-chloro-6-methyluracil | Sinbar | 5902-51-2 | DuPont | 16 | 0.17 | 710 |
| Triflusul-furonmethyl | Methyl 2-[[[[[(4-(dimethylamino)-6-(2,2,2-trifluoroethoxy)-1,3,5-triazin-2-yl]amino]carbonyl]amino]sulfonyl]-3-methylbenzoate | Upbeet | 126535-15-7 | DuPont | 33 | 0.3 | 110–11000 |

The herbicide may be added to the water in any convenient form, for example as a solid or liquid. Alternatively, when the herbicide is commercially available with a suitable carrier in the form of a formulation containing the herbicide, it may be added to the water in this form, provided that it has no undesirable effect upon the recirculating water system, for example, discoloration of the water or excessive foaming. Examples of formulated herbicides include solutions, dispersions, emulsions and micro-emulsions of the herbicide in various solvents, co-solvents and optionally with other additives, for example, dispersants, surfactants, emulsifying agents and adjuvants.

The present methods may utilize compositions containing a herbicide or a combination of two or more of the hereinbefore described herbicides. The addition of two or more herbicides to the recirculating water system can provide a broader spectrum of activity and/or provide increased efficacy against particularly problematic or nuisance algae.

The compositions of the present invention may comprise an agricultural fungicide as described hereinafter.

The Agricultural Fungicide

Fungicides are selected for use in agriculture based on factors such as their efficacy versus plant pathogens, uptake by and/or persistence on plants, and physical parameters associated with ease of formulation/application. Thus, the selection parameters differ significantly from those associated with the selection of a fungicide for a recirculating water system such as a swimming pool or a spa.

The agricultural fungicide for use in the compositions of the present invention is preferably sufficiently water-soluble to give a concentration of the fungicide in the recirculating water system which is sufficient to inhibit the growth of or kill algae present in the recirculating water system. When the fungicide is added to a recreational recirculating water system such as a swimming pool or spa, it is also preferable that it has sufficient water-solubility, so as not to adversely affect the appearance of the water in the recirculating water system, for example, by discoloring the water, causing water turbidity or excessive foaming.

Preferably, the agricultural fungicide has a water-solubility of at least 1 ppm, more preferably at least 2 ppm, especially at least 5 ppm, more especially at least 50 ppm, and particularly at least 100 ppm. The upper limit of the agricultural fungicide's water-solubility does not matter, although typically, the commercially available agricultural fungicides have a water-solubility below 100,000 ppm, and more usually below 25,000 ppm.

The solubility of many agricultural fungicides is influenced by pH. In recirculating water systems, the pH is preferably in the range of from about 6.5 to 9.0, more preferably from about 6.8 to 8.5, and especially from about 7.0 to 8.2. Accordingly, the above-mentioned preferred solubility of the agricultural fungicide is the solubility in water at the pH of the recirculating water system.

Examples of suitable agricultural fungicides which may be used either alone, in combination, or in conjunction with a herbicide used in the present invention include antifungal methoxycrylates, e.g. methyl (E)-2-2-6-(2-cyanophenoxy) pyrimidin-4-yloxyphenyl-3-methoxyacrylate; antifungal carboxamides, e.g. 5,6-dihydro-2-methyl-N-phenyl-1,4-oxathiin-3-carboxamide; antifungal aldehydes, e.g. cinnamaldehyde; antifungal thiocarbamates, e.g. S-ethyl cyclohexyl(ethyl)thiocarbamate; antifungal acetamides, e.g. 2-cyano-N-[(ethylamino)carbonyl]-2-(methoxyamino) acetamide; antifungal pyrimidines, e.g. 4-cyclopropyl-6-methyl-N-phenyl-2-pyrimidinamine and 5-butyl-2-ethylamino-6-methylpyrimidin-4-ol; antifungal morpholines, e.g. (E,Z)-4-[3-(4-chlorophenyl)-3-(3,4-dimethoxyphenyl)acryloyl]morpholine; antifungal guanidines, e.g. 1-dodecylguanidine acetate; antifungal pyrroles, e.g. 4-(2,2-difluoro-1 ,3-bezodioxol-4-yl)-1Hpyrrole-3-carbonitrile; antifungal imidazoles, e.g. 1-[2-(2,4-dichlorophenyl)-2-(2-propenyloxy)ethyl]-1H-imidazole and 3-(3,5-dichlorophenyl)-N-(1-methylethyl)-2,4-dioxo-1-imidazolidinecarboxamide; antifungal alanine derivatives, e.g. N-(2,6-dimethylphenyl)-N-(methoxyacetyl)-D-alaninemethyl ester and N-(2,6-dimethylphenyl)-N-(methoxyacetyl)-DL-alaninemethyl ester; antifungal carbamates, e.g. propyl 3-(dimethylamino) propylcarbamate-hydrochloride; antifungal triazoles, e.g. 1-[[2-(2,4-dichlorophenyl)-4-propyl-1,3-dioxolan-2-yl] methyl]-1H-1,2,4-triazole, H-1,2,4-triazole-1-ethanol-alpha-[2-(4-chlorophenyl)-ethyl]-alpha-(1,1-dimethylethyl), 1-(4-chlorophenoxy)-3,3-dimethyl-1-(1H-1,2,4-triazol-1-yl)-2-butanone and beta-(4-chlorophenoxy)-alpha-(1,1-dimethylethyl)-1-1H-1,2,4-triazole-1-ethanol, antifungal preferably less than 0.8, especially less than 0.5, and more especially less than 0.1, wherein the RfD value is as hereinbefore defined.

When an agricultural fungicide is used, it is preferably present in the recirculating water system at a concentration of from 0.1 to 24 ppm, more preferably from 0.2 to 1 5ppm, and especially from 0.5 to 10 ppm.

Preferably, the agricultural fungicide is such that, when incorporated in the water, the presence of the agricultural fungicide cannot be detected by the human nose (i.e. it is odorless or has no offensive odor). This is of particular relevance for recreational waters.

Examples of suitable agricultural fungicides for use in the present invention and their properties are shown in Table B below:

TABLE B

| Fungicide | Chemical Name | Trade Name | CAS Number | Suppliers | Margin of Exposure vs NOEL | Margin of Exposure vs. RfD | Solubility mg/l |
|---|---|---|---|---|---|---|---|
| Azoxystrobin | Methyl (E)-2-2-6-(2-cyanophenoxy)pyrimidin-4-yloxyphenyl-3-methoxyacrylate | Heritage | 131860-33-8 | Zeneca Ag | 240 | 2.4 | 10 |
| Carboxin | 5,6-dihydro-2-methyl-N-phenyl-1,4-oxathiin-3-carboxamide | Vitavax | 5234-68-4 | Uniroyal | 116 | 1.2 | 170 |
| Cycloate | S-ethyl cyclohexyl(ethyl)thiocarbamate | Ro-Neet | 1134-23-2 | Zeneca | 1 | 0.001 | 75 |
| Cymoxanil | 2-cyano-N-[(ethylamino)carbonyl]-2-(methoxyamino)acetamide | Curzate | 57966-95-7 | DuPont | | | 1000 |
| Cyprodinil | 4-cyclopropyl-6-methyl-N-phenyl-2-pyrimidinamine | Vangard | 121552-61-2 | Novartis | 50 | 0.5 | 13–20 |
| Dimethomorph | (E,Z)-4-[3-(4-chlorophenyl)-3-(3,4-dimethoxyphenyl)acryloyl]morpholine | Acrobat | 110488-70-5 | American Cyanamid | 88 | 0.8 | 50 |
| Dodine | 1-dodecylguanidine acetate | Carpene | 2439-10-3 | Rhone Poulenc | 17 | 0.02 | 63 |
| Ethirimol | 5-butyl-2-ethylamino-6-methylpyrimidin-4-ol | ??? | 23947-60-6 | Zeneca | | | 250 |
| Fludioxonil | 4-(2,2-difluoro-1,3-bezodioxol-4-yl)-1Hpyrrole-3-carbonitrile | Maxim | 13141-86-1 | Novartis | 44 | 0.4 | |
| Imazalil | 1-[2-(2,4-dichlorophenyl)-2-(2-propenyloxy)ethyl]-1H-imidazole | Fungazil | 35554-44-0 | Janssen Pharmaceutica | 17 | 0.2 | 1400 |
| Iprodione | 3-(3,5-dichlorophenyl)-N-(1-methylethyl)-2,4-dioxo-1-imidazolidinecarboxamide | Chipco | 36734-19-7 | Rhone Poulenc | 81 | 0.3 | 13 |
| mefenoxam | N-(2,6-dimethylphenyl)-N-(methoxyacetyl)-D-alaninemethyl ester | Ridomil Gold | | Novartis | | | |
| Metalaxyl | N-(2,6-dimethylphenyl)-N-(methoxyacetyl)-DL-alaninemethyl ester | Ridomil or Subdue | 57837-19-1 | Novartis | 98 | 1 | 8400 |
| Propamocarb | Propyl 3-(dimethylamino)propylcarbamate-hydrochloride | Banol | 25606-41-1 | AgrEvro USA Co. | 438 | 1.4 | |
| Propiconazole | 1-[[2-(2,4-dichlorophenyl)-4-propyl-1,3-dioxolan-2-yl]methyl]-1H-1,2,4-triazole | Banner | 60207-90-1 | Ciba-Geigy | No Data | No Data | 100 |
| Tebuconazole | H-1,2,4-triazole-1-ethanol-alpha-[2-(4-chlorophenyl)-ethyl]-alpha-(1,1-dimethylethyl) | Folicur | 107534-96-3 | Bayer | 13 | 0.4 | |
| Triademefon | 1-(4-chlorophenoxy)-3,3-dimethyl-1-(1H-1,2,4-triazol-1-yl)-2-butanone | Bayleton | 43121-43-3 | Bayer | 104 | 0.4 | 260 |
| Triademenol | Beta-(4-chlorophenoxy)-alpha-(1,1-dimethylethyl)-1-1H-1,2,4-triazole-1-ethanol | Baytan | 55219-65-3 | Bayer | 50 | 0.5 | 260 |
| Vinclozolin | 3-(3,5-dichlorophenyl)-5-methyl-5-vinyl-1,3-oxazolidine-2,4-dione | Ronilan | 50471-44-8 | BASF | 33 | 0.3 | 2.6 | oxazolidines, e.g. 3-(3,5-dichlorophenyl)-5-methyl-5-vinyl-1,3-oxazolidine-2,4-dione or a mixture of two or more thereof.

Preferably, the agricultural fungicide contains a propyl or isopropyl group.

The preferred agricultural fungicide has a margin of exposure versus NOEL value of greater than 10, more preferably greater than 50, especially greater than 80, more especially greater then 99, wherein the NOEL value is as hereinbefore defined.

Preferably, the agricultural fungicide preferably has a margin of exposure versus RfD value of less than 1, more The agricultural fungicide may be added to the water in any convenient form, for example as a solid or liquid. Alternatively, when the agricultural fungicide is commercially available with a suitable carrier in the form of a formulation containing the fungicide, it may be added to the water in this form provided that it has no undesirable effect upon the recirculating water system, for example discoloration of the water. Examples of formulated agricultural fungicides include solutions, dispersions, emulsions and microemulsions of the agricultural fungicide in various solvents, co-solvents and optionally other additives, for example dispersants, surfactants, emulsifying agents and adjuvants.

The present methods may utilize compositions containing an agricultural fungicide or a combination of two or more of the hereinbefore described agricultural fungicides. The addition of two or more agricultural fungicides to the recirculating water system can provide a broader spectrum of activity and/or provide increased efficacy against algae, particularly nuisance algae.

In addition, the agricultural fungicide having anti-algal activity may also advantageously be used in combination with a herbicide having anti-algal activity in recirculating water systems, as described above, to enhance the efficacy of the compositions and methods of the present invention.

Recirculating Water System

The present invention is applicable to and suitable for use in any industrial or recreational recirculating water system, but is especially suitable for recreational recirculating water systems. Examples of industrial water systems which can benefit by way of the present invention include heating and cooling systems, e.g. cooling towers and domestic central heating systems. Examples of recreational recirculating water systems include swimming pools, spas, jacuzzis and ornamental ponds.

Sanitizing Agent

Preferably, the compositions and methods of the present invention further comprise adding a sanitizing agent to the water system, thereby inhibiting the growth of or killing bacteria, particularly bacterial pathogens, and other microorganisms. The pathogenic bacteria of concern in recirculating waters include but are not limited to *Escherichia coli*, Staphlococcus auerus, Pseudomonas aeruginosa, and *Enterobacter faecalis*.

The sanitizing agent may be any sanitizing agent which inhibits the growth of bacteria, especially pathogens and potential pathogens, and other microorganisms. In recreational recirculating water systems, suitable examples of sanitizing agents include for example but are not limited to chlorine, bromine, ozone, hydrogen peroxide, calcium hypochlorite, sodium hypochlorite, lithium hypochlorite, a chlorine release agent (preferably a chlorinated isocyanurate, or a chlorinated hydantoin, more preferably dichlorocyanuric acid or trichlorocyanuric acid), a bromine release agent, a hydrogen peroxide release agent, an ozone release agent, water-soluble copper or silver or chelated copper salts, (e.g. copper sulphate, chelated copper sulphate), quaternary ammonium salts, and biguanides, especially a polymeric biguanide or a mixture thereof. In industrial systems where the toxicity of the agent is not as important, other sanitizers may be also be suitable, for example but not limited to 2-methylisothiazolinone, 5-chloro-2-methylisothiazolinone, benzisothiazolinone, 2-bromo-2-nitropropane-1,3-diol, 1,2-dibromo-2,4-dicyanobutane, methylene bisthiocyanate, 2-(thiocyanomethylthio)-benzothiazole, formaldehyde and formaldehyde release agents, glutaraldehyde, dibromonitrilopropionamide and bromo-hydroxyacetophenone or mixtures thereof.

Preferred sanitizing agents are a biguanide, especially a polymeric biquanide such as PHMB, bromine, chlorine or a chlorine release agent.

When the sanitizing agent is chlorine or a chlorine release agent, it is preferably added to the recirculating water system to provide a concentration of free available chlorine in the water in the range of from about 0.2 to 100 ppm, more preferably about 0.2 to 24 ppm, especially about 0.3 to 10 ppm, and more especially about 0.5 to 5.0 ppm.

The term "free available chlorine" refers to the amount of hypochlorous acid and hypochlorite ion found in the water. The concentration of free available chlorine may be determined using the Standard Methods for the Examination of Water and Wastewater, Method 4500-Cl G DPD Colorimetric Method.

When the sanitizing agent is a polymeric biguanide, it is preferably added to the recirculating water system to provide a concentration thereof in the range of about 1 to 20 ppm, more preferably about 4 to 15 ppm, especially about 5 to 12 ppm, and more especially about 6 to 10 ppm.

It is especially preferred that the sanitizing agent is a polymeric biguanide because we have found that a combination of a polymeric biguanide (especially PHMB) with a herbicide or an agricultural fungicide (or combinations thereof) provides particularly effective control over the growth of bacteria and nuisance algae, so as to advantageously provide a broader spectrum of antimicrobial activity in the recirculating waters.

The preferred polymeric biguanide preferably contains at least two biguanide units of Formula (1):

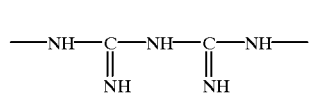

(1)

linked by a bridging group which contains at least one methylene group. The bridging group preferably includes a polymethylene chain, optionally incorporating or substituted by one or more hetero atoms such as oxygen, sulphur or nitrogen. The bridging group may include one or more cyclic nuclei which may be saturated or unsaturated. Preferably, the bridging group is such that there are at least three, and especially at least four, carbon atoms directly interposed between two adjacent biguanide units of Formula (1). Preferably, there are not greater than 10 and especially not greater than eight carbon atoms interposed between two adjacent biguanide units of Formula (1).

The polymeric biguanide may be terminated by any suitable group, such as hydrocarbyl or substituted hydrocarbyl or by amino or by a cyanoguanidine group of the formula:

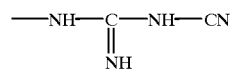

When the terminating group is hydrocarbyl, it is preferably alkyl, cycloalkyl or aralkyl. When the terminating group is substituted hydrocarbyl, the substituent may be any substituent that does not exhibit undesirable adverse effects on the microbiological properties of the polymeric biguanide. Examples of such substituents are aryloxy, alkoxy, acyl, acyloxy, halogen and nitrile.

When the polymeric biguanide contains two biguanide groups of Formula (1), the two biguanide groups are preferably linked through a polymethylene group, especially a hexamethylene group and the biguanide is a bisbiguanide, The terminating groups in such bisbiguanides are preferably $C_{1-10}$-alkyl which may be linear or branched and optionally substituted aryl, especially optionally substituted phenyl. Examples of such terminating groups are 2-ethylhexyl and 4-chlorophenyl. Specific examples of such bisbiguanides are compounds represented by Formula (2) and (3) in the free base form:

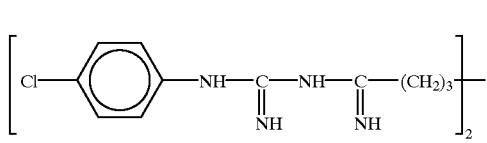
(2)

and

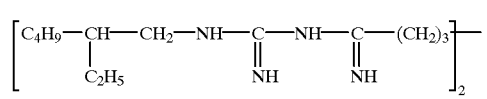
(3)

The polymeric biguanide preferably contains more than two biguanide units of Formula (1) and is preferably a linear polymeric biguanide which has a recurring polymeric chain represented by Formula (4) or a salt thereof:

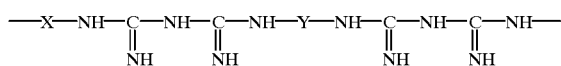
(4)

wherein X and Y represent bridging groups in which together the total number of carbon atoms directly interposed between the pairs of nitrogen atoms linked by X and Y is more than 9 and less than 17.

The bridging groups X and Y preferably comprise of polymethylene chains, optionally interrupted by hetero atoms, for example, oxygen, sulphur or nitrogen. X and Y may also incorporate cyclic nuclei which may be saturated or unsaturated, in which case the number of carbon atoms directly interposed between the pairs of nitrogen atoms linked by X and Y is taken as including that segment of the cyclic group, or groups, which is the shortest. Thus, the number of carbon atoms directly interposed between the nitrogen atoms in the group

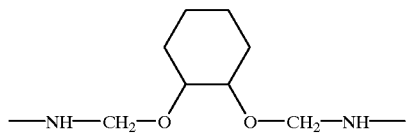

is 4 and not 8.

The linear polymeric biguanides having a recurring polymer unit of Formula (4) are typically obtained as mixtures of polymers in which the polymer chains are of different lengths. Preferably, the number of individual biguanide units of formulae:

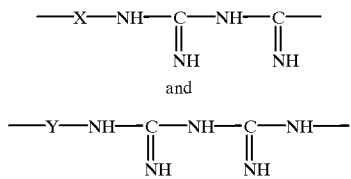

is, together, from 3 to about 80.

The preferred linear polymeric biguanide is a mixture of polymer chains in which the individual polymer chains, excluding the terminating groups, are of the Formula (5) or a salt thereof:

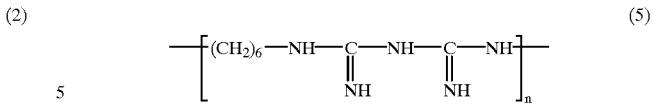
(5)

wherein n is from 4 to 40 and especially from 4 to 15. It is especially preferred that the average value of n is about 12. Preferably, the average molecular weight of the polymer in the free base form is from 1100 to 3300.

The linear polymeric biguanides may be prepared by the reaction of a bisdicyandiamide having the formula:

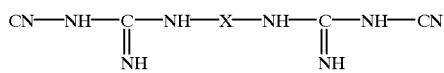

with a diamine $H_2N-Y-NH_2$, wherein X and Y have the meanings defined above or by reaction between a diamine salt or dicyanimide having the formula:

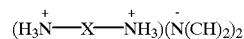

with a diamine $H_2N-Y-NH_2$ wherein X and Y have the meanings defined above. These methods of preparation are described in UK specifications numbers 702,268 and 1,152,243 respectively, and any of the polymeric biguanides described therein may be used.

As noted hereinbefore, the polymer chains of the linear polymeric biguanides may be terminated either by an amino group or by a cyanoguanidine group:

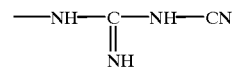

This cyanoguanidine group can hydrolyse during preparation of the linear polymeric biguanide yielding a guanidine end group. The terminating groups may be the same or different on each polymer chain.

A small proportion of a primary amine $R—NH_2$, where R represents an alkyl group containing from 1 to 18 carbon atoms, may be included with the diamine $H_2N—Y—NH_2$ in the preparation of polymeric biguanides as described above. The primary amine acts as a chain-terminating agent and consequently one or both ends of the polymeric biguanide polymer chains may be terminated by an —NHR group. These —NHR chain-terminated polymeric biguanides may also be used.

The polymeric biguanides readily form salts with both inorganic and organic acids. Preferred salts of the polymeric biguanide are water-soluble. When the polymeric biguanide is represented by a compound of Formula (2) in the free base form, a preferred water soluble salt is the digluconate. When the polymeric biguanide is represented by a compound of Formula (3) in the free base form, a preferred water soluble salt is the diacetate and where the much preferred polymeric biguanide is a mixture of linear polymers represented by Formula (5) in the free base form, the preferred salt is the hydrochloride.

It is especially preferred that the polymeric biguanide is a mixture of linear polymers, the individual polymer chains of which, excluding the terminating groups, are represented by Formula (5) in the hydrochloride salt form. This is commercially available from Avecia Inc. under the trademark BAQUACIL®.

Another aspect then of the present invention comprises a method for inhibiting the growth of or killing algae and bacteria in a recirculating water system, preferably a recreational recirculating water system, which method comprises adding to the water in either order or simultaneously:

(i) a compound having anti-algal activity selected from the group consisting of a herbicide and an agricultural fungicide or a combination thereof; and (ii) a sanitizing agent.

The sanitizing agent can be, for example, bromine, chlorine, a chlorine release agent, and a biguanide, particularly a polymeric biguanide, especially PHMB.

The compound having anti-algal activity is added to the water system to provide a concentration thereof sufficient to inhibit the growth of or kill algae and the sanitizing agent is added to the water system to provide a concentration thereof sufficient to inhibit the growth of or kill bacteria and other microorganisms, particularly bacterial pathogens.

In this preferred embodiment, the concentration of sanitizing agent utilized will depend upon the compound used. As hereinbefore described, when the sanitizing agent is chlorine, the concentration of free available chlorine is preferably in the range of from 0.2 to 100 ppm, more preferably from 0.5 to 5 ppm. When the sanitizing agent is a polymeric biguanide, such as PHMB, it is preferably present at a concentration of from 1 to 20 ppm, more preferably from 6 to 10 ppm.

The amount of the compound having anti-algal activity may range from about 0.1 to 24 ppm; preferably about 0.2 to 15 ppm; and more especially about 0.5 to 10 ppm.

In specific embodiments of the compositions of the present invention, the herbicide, the concentration of herbicide, the sanitizer and the concentration of sanitizer in the water are as shown respectively in Table C below:

TABLE C

| Herbicide | Concentration of herbicide (ppm) | Sanitizer | Concentration of Santiser (ppm) |
|---|---|---|---|
| 2-chloro-2',6'-diethyl-N-(methoxymethyl) acetanilide | 0.1 to 1000 | PHMB | 0 to 1000 |
| 2-ethylamino-4-isopropylamino-6-methylthio-s-triazine | 0.1 to 50 | PHMB | 1 to 100 |
| Methyl 2-[[[[[(4,6-dimethoxypyrimidin-2-yl)amino]carbonyl]amino]sulfonyl]methyl]benzoate | 0.2 to 10 | PHMB | 1 to 12 |
| 3-isopropyl-1H-2,1,3-benzothiadiazin-4(3H)-one 2,2-dioxide | 3 to 15 | PHMB | 0 to 10 |
| Ethyl a, 2-dichloro-5-[4-(difluoromethyl)-4,5-dihydro-3-methyl-5-oxo-1H-1,2,4-triazol-1-yl]-4-fluorobenzenepropanoate | 0.2 to 12 | PHMB | 0.1 to 10 |
| 5-amino-4-chloro-2-phenyl-3(2H)-pyridazinone | 0 | PHMB | |
| Ethyl-2-[[[[(4-chloro-6-methoxy-2-pyrimidinyl)amino]-carbonyl]amino]sulfonyl]benzoate | 5 to 25 | PHMB | 5 to 20 |
| 3-[p-(p-chlorophenoxy)phenyl]-1,1-di-methylurea | 3 to 15 | PHMB | 0.1 to 12 |
| Isopropyl 3-chlorocarbanilate | 10 to 12 | PHMB | |
| 2-chloro-N-[[(4-methoxy-6-methyl-1,3,5-triazin-2-yl)amino]carbonyl]benzenesulfonamide | 1 to 5 | PHMB | 1 to 10 |
| 2-[(2-chlorophenyl)methyl]-4,4-dimethyl-3-isoxazolidinone | 2 to 15 | PHMB | 0.5 to 5 |
| Isopropyl 3-chlorophenylcarbamate | 0.1 to 10 | PHMB | 0.2 to 15 |
| 2,6-diclorobenzonitrile | 0.5 to 5 | PHMB | 0.1 to 25 |
| 7-oxabicyclo[2,2,1]heptane-2,3-dicarboxylic acid | 0.1 to 3 | PHMB | 0.5 to 5 |
| Methyl 5-{[(4,6-dimethoxy-2-pyrimidinyl)amino]carbonylaminosulfonyl}-3-chloro-1-methyl-1H-pyrazole-4-carboxylate | 0.5 to 10 | PHMB | 0 to 10 |
| 3-cyclohexyl-6-(dimethylamino)-1-methyl-1,3,5-triazine-2,4(1H,3H)-dione | 1 to 15 | PHMB | 0.3 to 10 |
| 2-[4,5-dihydro-4-methyl-4-(1-methylethyl)-5-oxo-1H-imidazol-2-yl]-5ethyl-3-pyridinecarboxylic acid | 3 to 15 | PHMB | 1 to 5 |
| 4-amino-6-(1,1-dimethylethyl)-3-(methylthio)-1,2,4-triazin-5(4H)-one | 0.1 to 10 | PHMB | 0.1 to 10 |
| Methyl 2-[[[[(4-methoxy-6-methyl-1,3,5-triazin-2-yl)amino]carbonyl]amino]sulfonyl]benzoate | 3 to 17 | PHMB | 1 to 10 |
| S-ethyl hexahydro-1H-azepine-1-carbothioate | 0.5 to 2 | PHMB | 0.1 to 15 |
| 6-chloro-N-methyl-N'-(1-methylethyl)-1,3,5-triazine-2,4-diamine | 3 to 7 | PHMB | 0.5 to 10 |
| S-Propyl butyl(ethyl)thiocarbamate | 0.1 to 2 | PHMB | 0.5 to 5 |
| N,N'-bis(1-methylethyl)-6-(methylthio)-1,3,5-triazine-2,4-diamine | 1 to 10 | PHMB | 1 to 15 |
| N-(3,4-dichlorophenyl)propanamide | 0.2 to 20 | PHMB | 0.1 to 24 |
| 1-methylethylphenyl carbamate | 0.1 to 50 | PHMB | 0.1 to 10 |
| 2-[1-(ethoxyimino)butyl]-5-[2-(ethylthio)propyl]-3-hydroxy-2-cyclohexen-1-one | 0.5 to 20 | PHMB | 0.5 to 12 |
| 3-tert-Butyl-5-chloro-6-methyluracil | 3 to 9 | PHMB | 0.1 to 10 |
| Methyl 2-[[[[-(4-(dimethylamino)-6-(2,2,2-trifluoroethoxy)-1,3,5-triazin-2-yl]amino]carbonyl]amino]sulfonyl]-3-methylbenzoate | 5 to 10 | PHMB | 0.5 to 5 |
| 2-chloro-2',6'-diethyl-N-(methoxymethyl) acetanilide | 0.1 to 1000 | Chlorine | 0 to 1000 |
| 2-ethylamino-4-isopropylamino-6-methylthio-s-triazine | 0.1 to 50 | Chlorine | 1 to 100 |
| Methyl 2-[[[[[(4,6-dimethoxypyrimidin-2-yl)amino]carbonyl]amino]sulfonyl]methyl]benzoate | 0.2 to 10 | Chlorine | 1 to 12 |
| 3-isopropyl-1H-2,1,3-benzothiadiazin-4(3H)-one 2,2-dioxide | 3 to 15 | Chlorine | 0 to 10 |
| Ethyl a, 2-dichloro-5-[4-(difluoromethyl)-4,5-dihydro-3-methyl-5-oxo-1H-1,2,4-triazol-1-yl]-4-fluorobenzenepropanoate | 0.2 to 12 | Chlorine | 0.1 to 10 |
| 5-amino-4-chloro-2-phenyl-3(2H)-pyridazinone | 0 | Chlorine | |
| Ethyl-2-[[[[(4-chloro-6-methoxy-2-pyrimidinyl)amino]-carbonyl]amino]sulfonyl]benzoate | 5 to 25 | Chlorine | 5 to 20 |

TABLE C-continued

| Herbicide | Concentration of herbicide (ppm) | Sanitizer | Concentration of Santiser (ppm) |
|---|---|---|---|
| 3-[p-(p-chlorophenoxy)phenyl]-1,1-di-methylurea | 3 to 15 | Chlorine | 0.1 to 12 |
| Isopropyl 3-chlorocarbanilate | 10 to 12 | Chlorine | |
| 2-chloro-N-[[(4-methoxy-6-methyl-1,3,5-triazin-2-yl)amino]carbonyl]benzenesulfonamide | 1 to 5 | Chlorine | 1 to 10 |
| 2-[(2-chlorophenyl)methyl]-4,4-dimethyl-3-isoxazolidinone | 2 to 15 | Chlorine | 0.5 to 5 |
| Isopropyl 3-chlorophenylcarbamate | 0.1 to 10 | Chlorine | 0.2 to 15 |
| 2,6-diclorobenzonitrile | 0.5 to 5 | Chlorine | 0.1 to 25 |
| 7-oxabicyclo[2,2,1]heptane-2,3-dicarboxylic acid | 0.1 to 3 | Chlorine | 0.5 to 5 |
| Methyl 5-{[(4,6-dimethoxy-2-pyrimidinyl)amino]carbonylaminosulfonyl}-3-chloro-1-methyl-1H-pyrazole-4-carboxylate | 0.5 to 10 | Chlorine | 0 to 10 |
| 3-cyclohexyl-6-(dimethylamino)-1-methyl-1,3,5-triazine-2,4(1H,3H)-dione | 1 to 15 | Chlorine | 0.3 to 10 |
| 2-[4,5-dihydro-4-methyl-4-(1-methylethyl)-5-oxo-1H-imidazol-2-yl]-5ethyl-3-pyridinecarboxylic acid | 3 to 15 | Chlorine | 1 to 5 |
| 4-amino-6-(1,1-dimethylethyl)-3-(methylthio)-1,2,4-triazin-5(4H)-one | 0.1 to 10 | Chlorine | 0.1 to 10 |
| Methyl 2-[[[[(4-methoxy-6-methyl-1,3,5-triazin-2-yl)amino]carbonyl]amino]sulfonyl]benzoate | 3 to 17 | Chlorine | 1 to 10 |
| S-ethyl hexahydro-1H-azepine-1-carbothioate | 0.5 to 2 | Chlorine | 0.1 to 15 |
| 6-chloro-N-methyl-N'-(1-methylethyl)-1,3,5-triazine-2,4-diamine | 3 to 7 | Chlorine | 0.5 to 10 |
| S-Propyl butyl(ethyl)thiocarbamate | 0.1 to 2 | Chlorine | 0.5 to 5 |
| N,N'-bis(1-methylethyl)-6-(methylthio)-1,3,5-triazine-2,4-diamine | 1 to 10 | Chlorine | 1 to 15 |
| N-(3,4-dichlorophenyl)propanamide | 0.2 to 20 | Chlorine | 0.1 to 24 |
| 1-methylethylphenyl carbamate | 0.1 to 50 | Chlorine | 0.1 to 10 |
| 2-[1-(ethoxylmino)butyl]-5-[2-(ethylthio)propyl]-3-hydroxy-2-cyclohexen-1-one | 0.5 to 20 | Chlorine | 0.5 to 12 |
| 3-tert-Butyl-5-chloro-6-methyluracil | 3 to 9 | Chlorine | 0.1 to 10 |
| Methyl 2-[[[[(4-(dimethylamino)-6-(2-2,2-trifluoroethoxy)-1,3,5-triazin-2-yl]amino]carbonyl]amino]sulfonyl]-3-methylbenzoate | 5 to 10 | Chlorine | 0.5 to 5 |
| 2-chloro-2'-6'-diethyl-N-(methoxymethyl) acetanilide | 0.1 to 1000 | Ozone | 0 to 1000 |
| 2-ethylamino-4-isopropylamino-6-methylthio-s-triazine | 0.1 to 50 | Ozone | 1 to 100 |
| Methyl 2-[[[[(4,6-dimethoxypyrimidin-2-yl)amino]carbonyl]amino]sulfonyl]methyl]benzoate | 0.2 to 10 | Ozone | 1 to 12 |
| 3-isopropyl-1H-2,1,3-benzothiadiazin-4(3H)-one 2,2-dioxide | 3 to 15 | Ozone | 0 to 10 |
| Ethyl a, 2-dichloro-5-[4-(difluoromethyl)-4,5-dihydro-3-methyl-5-oxo-1H-1,2,4-triazol-1-yl]-4-fluorobenzenepropanoate | 0.2 to 12 | Ozone | 0.1 to 10 |
| 5-amino-4-chloro-2-phenyl-3(2H)-pyridazinone | 0 | Ozone | |
| Ethyl-2-[[[[(4-chloro-6-methoxy-2-pyrimidinyl)amino]-carbonyl]amino]sulfonyl]benzoate | 5 to 25 | Ozone | 5 to 20 |
| 3-[p-(p-chlorophenoxy)phenyl]-1,1-di-methylurea | 3 to 15 | Ozone | 0.1 to 12 |
| Isopropyl 3-chlorocarbanilate | 10 to 12 | Ozone | |
| 2-chloro-N-[[(4-methoxy-6-methyl-1,3,5-triazin-2-yl)amino]carbonyl]benzenesulfonamide | 1 to 5 | Ozone | 1 to 10 |
| 2-[(2-chlorophenyl)methyl]-4,4-dimethyl-3-isoxazolidinone | 2 to 15 | Ozone | 0.5 to 5 |
| Isopropyl 3-chlorophenylcarbamate | 0.1 to 10 | Bromine | 0.2 to 15 |
| 2,6-diclorobenzonitrile | 0.5 to 5 | Bromine | 0.1 to 25 |
| 7-oxabicyclo[2,2,1]heptane-2,3-dicarboxylic acid | 0.1 to 3 | Bromine | 0.5 to 5 |
| Methyl 5-{[(4,6-dimethoxy-2-pyrimidinyl)amino]carbonylaminosulfonyl}-3-chloro-1-methyl-1H-pyrazole-4-carboxylate | 0.5 to 10 | Bromine | 0 to 10 |
| 3-cyclohexyl-6-(dimethylamino)-1-methyl-1,3,5-triazine-2,4(1H,3H)-dione | 1 to 15 | Bromine | 0.3 to 10 |
| 2-[4,5-dihydro-4-methyl-4-(1-methylethyl)-5-oxo-1H-imidazol-2-yl]-5ethyl-3-pyridinecarboxylic acid | 3 to 15 | Bromine | 1 to 5 |
| 4-amino-6-(1,1-dimethylethyl)-3-(methylthio)-1,2,4-triazin-5(4H)-one | 0.1 to 10 | Hydrogen peroxide | 0.1 to 10 |
| Methyl 2-[[[[(4-methoxy-6-methyl-1,3,5-triazin-2-yl)amino]carbonyl]amino]sulfonyl]benzoate | 3 to 17 | Hydrogen peroxide | 1 to 10 |
| S-ethyl hexahydro-1H-azepine-1-carbothioate | 0.5 to 2 | Hydrogen peroxide | 0.1 to 15 |
| 6-chloro-N-methyl-N'-(1-methylethyl)-1,3,5-triazine-2,4-diamine | 3 to 7 | Hydrogen peroxide | 0.5 to 10 |
| S-Propyl butyl(ethyl)thiocarbamate | 0.1 to 2 | Hydrogen peroxide | 0.5 to 5 |
| N,N'-bis(1-methylethyl)-6-(methylthio)-1,3,5-triazine-2,4-diamine | 1 to 10 | Hydrogen peroxide | 1 to 15 |
| N-(3,4-dichlorophenyl)propanamide | 0.2 to 20 | 5-chloro-2-methylisothiazolinone | 0.1 to 24 |
| 1-methylethylphenyl carbamate | 0.1 to 50 | 5-chloro-2-methylisothiazolinone | 0.1 to 10 |
| 2-[1-(ethoxylmino)butyl]-5-[2-(ethylthio)propyl]-3-hydroxy-2-cyclohexen-1-one | 0.5 to 20 | 5-chloro-2-methylisothiazolinone | 0.5 to 12 |
| 3-tert-Butyl-5-chloro-6-methyluracil | 3 to 9 | 5-chloro-2-methylisothiazolinone | 0.1 to 10 |
| Methyl 2-[[[[(4-(dimethylamino)-6-(2,2,2-trifluoroethoxy)-1,3,5-triazin-2-yl]amino]carbonyl]amino]sulfonyl]-3-methylbenzoate | 5 to 10 | 5-chloro-2-methylisothiazolinone | 0.5 to 5 |

In specific embodiments of the compositions of the present invention, the agricultural fungicide, the concentration of agricultural fungicide, the sanitizing agent and the concentration of the sanitizing agent in the water are as shown respectively in Table D below:

TABLE D

| Agricultural Fungicide | Concentration of fungicide (ppm) | Sanitiser | Concentration of Santiser (ppm) |
|---|---|---|---|
| Methyl (E)-2-2-6-(2-cyanophenoxy)pyrimidin-4-yloxyphenyl-3-methoxyacrylate | 0.1 to 1000 | PHMB | 0 to 1000 |
| 5,6-dihydro-2-methyl-N-phenyl-1,4-oxathiin-3-carboxamide | 0.1 to 50 | PHMB | 1 to 100 |
| S-ethyl cyclohexyl(ethyl)thiocarbamate | 0.2 to 10 | PHMB | 1 to 12 |
| 2-cyano-N-[(ethylamino)carbonyl]-2-(methoxyamino)acetamide | 3 to 15 | PHMB | 0 to 10 |
| 4-cyclopropyl-6-methyl-N-phenyl-2-pyrimidinamine | 0.2 to 12 | PHMB | 0.1 to 10 |
| (E,Z)-4-[3-(4-chlorophenyl)-3-(3,4-dimethoxyphenyl)acryloyl]morpholine | 0 | PHMB | |
| 1-dodecylguanidine acetate | 5 to 25 | PHMB | 5 to 20 |
| 5-butyl-2-ethylamino-6-methylpyrimidin-4-ol | 3 to 15 | PHMB | 0.1 to 12 |
| 4-(2,2-difluoro-1,3-bezodioxol-4-yl)-1Hpyrrole-3-carbonitrile | 10 to 12 | PHMB | |
| 1-[2-(24-dichlorophenyl)-2-(2-propenyloxy)ethyl]-1H-imidazole | 1 to 5 | PHMB | 1 to 10 |
| 3-(3,5-dichlorophenyl)-N-(1-methylethyl)-2,4-dioxo-1-imidazolidinecarboxamide | 2 to 15 | PHMB | 0.5 to 5 |
| N-(2,6-dimethylphenyl)-N-(methoxyacetyl)-D-alaninemethyl ester | 0.1 to 10 | PHMB | 0.2 to 15 |
| N-(2,6-dimethylphenyl)-N-(methoxyacetyl)-DL-alaninemethyl ester | 0.5 to 5 | PHMB | 0.1 to 25 |
| Propyl 3-(dimethylamino)propylcarbamate-hydrochloride | 0.1 to 3 | PHMB | 0.5 to 5 |
| 1-[[2-(2,4-dichlorophenyl)-4-propyl-1,3-dioxolan-2-yl]methyl]-1H-1,2,4-triazole | 0.5 to 10 | PHMB | 0 to 10 |
| H-1,2,4-triazole-1-ethanol-alpha-[2-(4-chlorophenyl)-ethyl]-alpha-(1,1-dimethylethyl) | 1 to 15 | PHMB | 0.3 to 10 |
| 1-(4-chlorophenoxy)-3,3-dimethyl-1-(1H-1,2,4-triazol-1-yl)-2-butanone | 3 to 15 | PHMB | 1 to 5 |
| Beta-(4-chlorophenoxy)-alpha-(1,1-dimethylethyl)-1-1H-1,2,4-triazole-1-ethanol | 0.1 to 10 | PHMB | 0.1 to 10 |
| 3-(3,5-dichlorophenyl)-5-methyl-5-vinyl-1,3-oxazolidine-2,4-dione | 3 to 17 | PHMB | 1 to 10 |
| Methyl (E)-2-2-6-(2-cyanophenoxy)pyrimidin-4-yloxyphenyl-3-methoxyacrylate | 0.1 to 1000 | Chlorine | 0 to 1000 |
| 5,6-dihydro-2-methyl-N-phenyl-1,4-oxathiin-3-carboxamide | 0.1 to 50 | Chlorine | 1 to 100 |
| S-ethyl cyclohexyl(ethyl)thiocarbamate | 0.2 to 10 | Chlorine | 1 to 12 |
| 2-cyano-N-[(ethylamino)carbonyl]-2-(methoxyamino)acetamide | 3 to 15 | Chlorine | 0 to 10 |
| 4-cyclopropyl-6-methyl-N-phenyl-2-pyrimidinamine | 0.2 to 12 | Chlorine | 0.1 to 10 |
| (E,Z)-4-[3-(4-chlorophenyl)-3-(3,4-dimethoxyphenyl)acryloyl]morpholine | 0 | Chlorine | |
| 1-dodecylguanidine acetate | 5 to 25 | Chlorine | 5 to 20 |
| 5-butyl-2-ethylamino-6-methylpyrimidin-4-ol | 3 to 15 | Chlorine | 0.1 to 12 |
| 4-(2,2-difluoro-1,3-bezodioxol-4-yl)-1Hpyrrole-3-carbonitrile | 10 to 12 | Chlorine | |
| 1-[2-(2,4-dichlorophenyl)-2-(2-propenyloxy)ethyl]-1H-imidazole | 1 to 5 | Chlorine | 1 to 10 |
| 3-(3,5-dichlorophenyl)-N-(1-methylethyl)-2,4-dioxo-1-imidazolidinecarboxamide | 2 to 15 | Chlorine | 0.5 to 5 |
| N-(2,6-dimethylphenyl)-N-(methoxyacetyl)-D-alaninemethyl ester | 0.1 to 10 | Chlorine | 0.2 to 15 |
| N-(2,6-dimethylphenyl)-N-(methoxyacetyl)-DL-alaninemethyl ester | 0.5 to 5 | Chlorine | 0.1 to 25 |
| Propyl 3-(dimethylamino)propylcarbamate-hydrochloride | 0.1 to 3 | Chlorine | 0.5 to 5 |
| 1-[[2-(2,4-dichlorophenyl)-4-propyl-1,3-dioxolan-2-yl]methyl]-1H-1,2,4-triazole | 0.5 to 10 | Chlorine | 0 to 10 |
| H-1,2,4-triazole-1-ethanol-alpha-[2-(4-chlorophenyl)-ethyl]-alpha-(1,1-dimethylethyl) | 1 to 15 | Chlorine | 0.3 to 10 |
| 1-(4-chlorophenoxy)-3,3-dimethyl-1-(1H-1,2,4-triazol-1-yl)-2-butanone | 3 to 15 | Chlorine | 1 to 5 |
| Beta-(4-chlorophenoxy)-alpha-(1,1-dimethylethyl)-1-1H-1,2,4-triazole-1-ethanol | 0.1 to 10 | Chlorine | 0.1 to 10 |
| 3-(3,5-dichlorophenyl)-5-methyl-5-vinyl-1,3-oxazolidine-2,4-dione | 3 to 17 | Chlorine | 1 to 10 |
| Methyl (E)-2-2-6-(2-cyanophenoxy)pyrimidin-4-yloxyphenyl-3-methoxyacrylate | 0.1 to 1000 | Ozone | 0 to 1000 |
| 5,6-dihydro-2-methyl-N-phenyl-1,4-oxathiin-3-carboxamide | 0.1 to 50 | Ozone | 1 to 100 |
| S-ethyl cyclohexyl (ethyl)thiocarbamate | 0.2 to 10 | Ozone | 1 to 12 |
| 2-cyano-N-[(ethylamino)carbonyl]2(methoxyamino)acetamide | 3 to 15 | Ozone | 0 to 10 |
| 4-cyclopropyl-6-methyl-N-phenyl-2-pyrimidinamine | 0.2 to 12 | Ozone | 0.1 to 10 |
| (E,Z)-4-[3-(4-chlorophenyl)-3-(3,4-dimethoxyphenyl)acrylol]morpholine | 0 | Ozone | |
| 1-dodecylguanidine acetate | 5 to 25 | Ozone | 5 to 20 |
| 5-butyl-2-ethylamino-6-methylpyrimidin-4-ol | 3 to 15 | Ozone | 0.1 to 12 |
| 4-(2,2-difluoro-1,3-bezodioxol-4-yl)-1Hpyrrole-3-carbonitrile | 10 to 12 | Ozone | |
| 1-[2-(2,4-dichlorophenyl)-2-(2-propenyloxy)ethyl]-1H-imidazole | 1 to 5 | Ozone | 1 to 10 |
| 3-(3,5-dichlorophenyl)-N-(1-methylethyl)-24-dioxo-1-imidazolidinecarboxamide | 2 to 15 | Bromine | 0.5 to 5 |
| N-(2,6-dimethylphenyl)-N-(methoxyacetyl)-D-alaninemethyl ester | 0.1 to 10 | Bromine | 0.2 to 15 |
| N-(2,6-dimethylphenyl)-N-(methoxyacetyl)-DL-alaninemethyl ester | 0.5 to 5 | Bromine | 0.1 to 25 |
| Propyl 3-(dimethylamino)propylcarbamate-hydrochloride | 0.1 to 3 | Bromine | 0.5 to 5 |
| 1-[[2-(2,4-dichlorophenyl)-4-propyl-1,3-dioxolan-2-yl]methyl]-1H-1,2,4-triazole | 0.5 to 10 | Bromine | 0 to 10 |
| H-1,2,4-triazole-1-ethanol-alpha-[2-(4-chlorophenyl)ethyl]-alpha(1,1-dimethylethyl) | 1 to 15 | Bromine | 0.3 to 10 |

TABLE D-continued

| Agricultural Fungicide | Concentration of fungicide (ppm) | Sanitiser | Concentration of Santiser (ppm) |
|---|---|---|---|
| 1-(4-chlorophenoxy)-3,3-dimethyl-1-(1H-1,2,4-triazol-1-yl)-2-butanone | 3 to 15 | Bromine | 1 to 5 |
| Beta-(4-chlorophenoxy)-alpha-(1,1-dimethylethyl)-1-1H-1,2,4-triazole-1-ethanol | 0.1 to 10 | Bromine | 0.1 to 10 |
| 3-(3,5-dichlorophenyl)-5-methyl-5-vinyl-1,3-oxazolidine-2,4-dione | 3 to 17 | Bromine | 1 to 10 |

In Tables C and D, when the sanitizing agent is indicated to be chlorine, the concentration of chlorine refers to the concentration of free available chlorine in the water as hereinbefore defined. The free available chlorine may be introduced from any convenient source, for example direct injection of chlorine, via a chlorine generator (e.g. electrolysis of sodium chloride), directly via sodium, calcium or lithium hypochlorite or by a chlorine release agent such as dichlorocyanuric acid or trichlorocyanuric acid.

Recirculating Water Systems

According to another aspect of the present invention, there is provided a recirculating water system comprising (i) water, (ii) a compound having anti-algal activity selected from the group consisting of a herbicide and an agricultural fungicide and combinations thereof and optionally a sanitizing agent; and (iii) means for recirculating the water; wherein the compound and sanitizing agent are dissolved in the water.

The suitable anti-algal compounds and sanitizing agents, their preferred amounts and the preferred water systems are as described above.

The preferred means for recirculating the water comprises a pump and equivalents thereof.

Compositions

According to another aspect the present invention, there is provided a composition suitable for use in recirculating water systems comprising:

(a) a compound having anti-algal activity selected from the group consisting of an herbicide and an agricultural fungicide and combinations thereof;

(b) a sanitizing agent; and (c) optionally water.

The ratio by weight of (a):(b) in the composition is preferably in the range of about 1 to 99, to 99 to 1, more preferably about 1 to 5 to 5 to 1, and especially about 1 to 2 to 2 to 1.

The total amount of component (a) preferably constitutes from about 1 to 99%, more preferably from about 5 to 50% by weight of the composition.

The suitable anti-algal compounds and sanitizing agents are as described above.

The compositions may be used to treat recirculating water systems, for example industrial and recreational recirculating water systems, to inhibit the growth of or kill algae, particularly nuisance algae.

Kits

According to yet another aspect of the present invention, there is provided a kit for treating a recirculating water system comprising:

(i) an anti-algal compound as described above;

(ii) a sanitizing agent; and (iii) instructions for adding (i) and (ii) to a recirculating water system, preferably to a swimming pool, spa, or an ornamental pond. The instructions preferably comprise directions as to how to use (i) and (ii) for the purpose of inhibiting the growth of and/or killing algae, especially nuisance algae as previously described, and bacteria, especially pathogenic bacteria.

In a preferred embodiment, the kit further comprises a means for determining the concentration of the anti-algal compound which has been added to the water of the recirculating water system. This enables a user of the kit to easily determine the appropriate concentration of anti-algal compound for the water system without undue experimentation, and how to maintain the concentration of the compound at the desired level.

It is especially suitable that the kit further comprises a means for determining the concentration of the sanitizing agent which has been added to the water of the recirculating water system.

The means for determining the concentration of the anti-algal compound and/or sanitizer may be any convenient means, for example, an indicator solution which gives a color change which varies in response to the concentration of the compound or sanitizer, respectively.

The invention is further illustrated by the following non-limiting examples in which all parts and percentages are by weight unless otherwise indicated.

EXAMPLES

Preventative Laboratory Studies on Algae

Preventative treatments, as the name implies, are intended to prevent an outbreak of algae from occurring. Without adequate control measures, outbreaks can occur in two different scenarios. In the first, the organism is present at all times but the concentration of the organism is so low that it is not noticeable. If a triggering event occurs, the organism reproduces rapidly resulting in a "bloom". Examples of triggering events are pH shifts, disturbance of a harboring biofilm in the filter or plumbing, and introduction of additional but previously limited nutrients, such as nitrogen.

In the other scenario, low numbers of organisms can be introduced into a previously non-colonized pool that has optimal growth conditions. The coincidence of organisms and optimal growth conditions can result in a "bloom". The organisms can be introduced by the fill water, atmospheric dust, rainfall, or by bathing suits that have been previously used in infected pools or rivers and not washed before re-use.

In preventative laboratory treatment studies, growth conditions are optimized to support a bloom. An experimental flask is prepared with a medium having optimized growth conditions to support a bloom. The medium in the flask is treated with a prescribed concentration of a test formulation, and then inoculated with a low concentration of a bloom-forming organism. The medium is monitored for a period of time to observe whether the formulation is effective at preventing the bloom.

These studies used the most problematic or nuisance algae, i.e. field isolated mustard algae. Any compound that shows good efficacy against mustard algae would be expected to provide even better control against the less environmentally-robust green and black algae.

Examples 1–3

A series of inocula of naturally occurring mustard algae was prepared by inoculating flasks of modified Jaworski's medium with unpurified wild algal isolates collected in the field and containing low levels of bacteria and culturing the flasks for two weeks. The Jaworski's medium was modified by the addition of 4 ppm PHMB to inhibit the growth of the bacteria present in the algal isolates. The inocula were pooled by aseptic vacuum filtration and the concentrated algal cell masses were combined ("pooled") and redispersed in an aseptic medium to provide a concentrated pooled inoculum. The amount of inoculum used was varied to achieve an initial optical density of 0.10 in the test flasks. The optical density was determined using a Milton Roy Spec 20 Spectrometer.

Test herbicides were assessed for anti-algal activity compared to known algaecides (quaternary ammonium compounds) and a blank control, by adding each herbicide or known algaecide at 10 ppm and 15 ppm to Jaworski's medium (50 ml) contained in 125 ml flasks containing 6 mm borosilicate beads (50). Each flask was then inoculated with a prescribed amount of the pooled inoculum, so that the liquid in the flask had no visible green cast. The flasks (including a control or blank containing no herbicide or known algaecide were closed with translucent caps and incubated at 27° C. for 10 days with 18 hours/day of illumination by a combination of fluorescent grow lamps and standard incandescent lamps. Algal growth was scored by visual observation on a scale of 0 to 4 and the results are shown in Table 1 below. A score of "1" indicates that the flask is slightly green. A score of "2" indicates moderate growth. A score of 3 means heavy growth. A score of "4" indicates that the flask is too turbid to see through. Any score >1 is considered a preventative failure.

TABLE 1

Preventive Algae Control

| | | Score @ ppm active agent | | | |
|---|---|---|---|---|---|
| Example | Active Agent | 0 | 10 | 15 | Comments |
| 1 | Clomazone | 4 | 4 | 3 | heavy growth |
| 2* | Metalochlor | 1 | 1 | 1 | very little growth |
| 3 | Terbacil | 0 | 0 | 0 | No visible growth or color |
| (Comparative) A | ADBAC# | 3 | 3 | 0 | Heavy growth No visible growth |
| (Comparative) B | Polyquat†# (WSCP ™) | 2 | 2 | 2 | Bloom noticeable |
| Control | Nil | | 4 | | very heavy growth |

Footnotes to Table 1
ADBAC - is alkyl dimethyl benzylammonium chloride
WSCP is Poly(oxyethylene(dimethylimino)-ethylene(dimethylimino)-ethylene dichloride) commercially available from Buckman Laboratories Inc.

Remedial Laboratory Studies on Algae Preamble

Remedial treatments are intended to reduce a bloom of algae once it has already occurred. During blooms, the algal infestation of the system is obvious, even to the casual observer. Effective remedial treatments are those that reduce the obvious symptoms, even if they do not result in a complete kill of the algae. Remedial treatments are considered effective if they return the system to a pre-bloom state.

Remedial efficacy was evaluated in these Examples using field isolated mustard algae. Any treatment showing good control of this organism is expected to display similar or even better efficacy against green and black algae.

Examples 4–16

Studies were conducted in 125 ml flasks containing 6 mm borosilicate glass beads (50) and Jaworski's medium (50 ml). The flasks were inoculated with pooled mid-log growth cultures of mustard algae to achieve an initial absorbance of 0.10, as measured using a Milton Roy Spec 20 Spectrometer. This concentration of algae in the water resulted in noticeable green color similar to that seen after brushing pools with moderate blooms. The herbicides identified in Table 2 were added at levels of 5 and 10 ppm active ingredient. The performance of the herbicides was compared to Control Examples A, B and C, respectively, with two EPA registered algaecides (ADBAC and Polyquat) and PHMB. The flasks were closed using translucent caps, illuminated for 18 hours using a combination of fluorescent grow lamps and standard incandescent lamps and incubated at 27° C. The algal growth was scored turbidimetrically. In this protocol, an increase of more than +0.05 units in turbidity at five days denoted that the algae was replicating rapidly. Under pool conditions, this is the equivalent of a full algal bloom. Changes of turbidity between +0.00 and +0.05 units tended to indicate antistatic activity wherein growth was suppressed but not necessarily killed. Decreases in turbidity were indications that the algae was being killed by the active agent. The results are shown in Table 2 below.

TABLE 2

Remedial Algae Control

| | | Change in Turbidity at active agent (ppm) five days post treatment | | |
|---|---|---|---|---|
| Example | Active Agent | 5 ppm | 10 ppm | comments |
| 4 | Dodine | −0.03 | −0.04 | algicidal activity |
| 5 | Hexazinone | −0.03 | −0.03 | algicidal activity |
| 6 | Propanil | −0.02 | −0.03 | algicidal activity |
| 7 | Terbacil | −0.02 | −0.02 | algicidal activity |
| 8 | cycolate | 0.00 | −0.01 | algicidal activity |
| 9 | carboxin | 0.01 | −0.01 | algicidal activity |
| 10 | bensulfuron-methyl | +0.01 | 0.00 | algicidal activity |
| 11 | chlorimuron | +0.03 | +0.02 | Algistatic. Considerably more effective than Controls C and D at 5 ppm. |
| 12 | triflusulfuron-methyl | +0.04 | +0.03 | Algistatic. Considerably more effective than Controls C and D at 5 ppm. |
| 13 | metsulfuron-methyl | +0.09 | +0.06 | Algistatic. More effective than Controls C and D at 5 ppm. |
| 14 | metolachlor | +0.12 | +0.06 | Algistatic. More effective than Controls D and very similar to Control C. |

TABLE 2-continued

Remedial Algae Control

| Example | Active Agent | Change in Turbidity at active agent (ppm) five days post treatment | | comments |
| --- | --- | --- | --- | --- |
| | | 5 ppm | 10 ppm | |
| 15 | chloridazon | +0.15 | +0.05 | Algistatic. More effective than Controls D and very similar to Control C. |
| 16 | Clomazone | +0.10 | +0.10 | more effective than Controls C and D at 5 ppm. This active shows improved control relative to those quats presently in use. |
| Control C Comparative | ADBAC# | +0.13 | +0.03 | This is 5x and 10x respectively the EPA allowable dosage level for ADBAC |
| Control D Comparative | Polyquat | +0.29 | +0.28 | This is a widely used EPA registered algaecide. It is not effective against mustard algae. |
| Control | 4 ppm PHMB# (Baquacil) | +0.32 | uncontrolled algal growth | |

Footnotes to Table 2
ADBAC is as described in Table 1.
PHMB is poly(hexamethylenebiguanide) hydrochloride, available as Baquacil ™ from Avecia Inc.

Table 2 clearly shows that even at 5× and 10 × the EPA allowable dose of ADBAC, no control of the mustard algae was observed. However, when the herbicides Hexazinone, Propanil, bensulfuronmethyl, and Terbacil and the agricultural fungicides Dodine, cycolate, and carboxin were used, the water turbidity decreased significantly indicating that these herbicides and fungicides were kililing the mustard algae.

Example 17

A series of inocula of naturally occurring mustard algae was prepared by inoculating flasks of modified Jaworski's medium with unpurified wild algal isolates collected in the field and containing low levels of bacteria and culturing the flasks for two weeks. The Jaworski's medium was modified by the addition of 4 ppm PHMB to inhibit the growth of the bacteria present in the algal isolates. The inocula were pooled by aseptic vacuum filtration and the concentrated algal cell masses were combined ("pooled") and redispersed in an aseptic medium to provide a concentrated pooled inoculum. The amount of inoculum used was varied to achieve an initial optical density of 0.10 in the test flasks. The optical density was determined using a Milton Roy Spec 20 Spectrometer.

Test agricultural fungicides were assessed for anti-algal activity compared to known algaecides (quaternary ammonium compounds) and a blank control, by adding each agricultural fungicide or known algaecide at 10 ppm and 15 ppm to Jaworski's medium (50 ml) contained in 125 ml flasks containing 6 mm borosilicate beads (50). Each flask was then inoculated with a prescribed amount of the pooled inoculum, so that the liquid in the flask had no visible green cast. The flasks (including a control or blank containing no agricultural fungicide or known algaecides were closed with translucent caps and incubated at 27° C. for 10 days with 18 hours/day of illumination by a combination of fluorescent grow lamps and standard incandescent lamps. Algal growth was scored by visual observation on a scale of 0 to 4 and the results are shown in Table 3 below. A score of "1" indicates that the flask is slightly green. A score of "2" indicates moderate growth. A score of 3 means heavy growth. A score of "4" indicates that the flasks are too turbid to see through. Any score >1 is considered a preventative failure.

Comparative Examples A, B and Control Example C employed two EPA registered algaecides (ADBAC—alkyl dimethyl benzylammonium chloride and WSCP—Poly(oxyethylene(dimethylimino)-ethylene(dimethylimino)-ethylene dichloride) and a control without any active agent.

TABLE 3

Visual score - Preventive Algae Control

| Ex. | Active Agent | Score @ 10 ppm | Score @ 15 ppm active ingredient | Comments |
| --- | --- | --- | --- | --- |
| 17 | Tebuconazole (Elite ™) | 2 | 1 | very little growth at 15 ppm |
| Comparative A | ADBAC | 3 | 0 | These concentrations are above the EPA allowable dose level, |
| Comparative B | Polyquat (WSCP ™) | 2 | 2 | These doses are in the EPA approved use range. |
| Control C | No active added Control | 4 | | very heavy growth |

Remedial lab studies on algae

Remedial treatments are intended to reduce a bloom of algae once it has already occurred. During blooms, the algal infestation of the system is readily obvious, even to the casual observer. Effective remedial treatments are those that reduce the obvious symptoms, even if they do not result in a complete kill of the algae. Remedial treatments are considered effective if they return the system to a pre-bloom state.

Remedial efficacy was evaluated in this Example using field isolated mustard algae. Any treatment showing good control of this organism is expected to display similar or even better efficacy against green and black algae.

Example 18

Studies were conducted in 125 ml flasks containing 6mm borosilicate glass beads (6mm) and 50 ml of Jaworski's medium. The flasks were inoculated with pooled mid-log growth cultures of mustard algae to achieve an initial absorbance of 0.10, as measured using a Milton Roy Spec 20 Spectrometer This concentration of algae in the water resulted in noticeable green color similar to that seen after brushing pools with moderate blooms. The agricultural fungicide identified in Table 4 was added at levels of 5 and 10 ppm active ingredient. The activity of the agricultural fungicide was compared in Control Examples A, B and C, respectively, with two EPA registered algaecides (ADBAC and polyquat) and one EPA registered sanitizer/algistat (PHMB). Flasks were closed with translucent caps, illuminated for 18 hours using a combination of fluorescent grow lamps and standard incandescent lamps and incubated at 27° C. Growth was scored turbidimetrically. In this protocol, an increase of more than +0.05 units in turbidity at five days denoted that the algae was replicating rapidly. Under pool conditions, this is the equivalent of full algal bloom. Changes of turbidity between +0.00 and +0.05 units tended to indicate antistatic activity wherein growth was suppressed but the algae were not necessarily killed. Decreases in turbidity were indications that the algae was being killed by the active agent. The results are shown in Table 4 below.

TABLE 4

Remedial Algae Control
Change in Turbidity at five days post treatment.

| Example | Active Agent (trade name) | Turbidity @ 5 ppm active ingredient | Turbidity @ 10 ppm active ingredient | comments |
|---|---|---|---|---|
| 18 | Tebuconazole (Elite) | +0.09 | +0.24 | more effective than Controls A and B at 5 ppm. |
| Control A | ADBAC (BaquaCheck 50) | +0.13 | +0.03 | These concentrations are above the EPA allowable dose level. |
| Control B | Polyquat (WSCP) | +0.29 | +0.28 | These doses are in the EPA approved use range. |
| Control C | 4 ppm PHMB (Baquacil ®) | +0.32 | | algae grew uncontrolled |

What we claim is:

1. A composition for controlling the growth of nuisance algae in a recirculating water system which composition comprises any of a herbicide having anti-algal activity in said water system, an agricultural fungicide having anti-algal activity in said water system or a combination thereof, and a sanitizing agent wherein,
   the fungicide is selected from the group consisting of antifungal methoxyacrylates, antifungal carboxamides, antifungal aldehydes, antifungal thiocarbamates, antifungal acetamides, antifungal pyrimidines, antifungal morpholines, antifungal guanidines, antifungal imidazoles, antifungal carbamate, antifungal oxazolidine, antifungal pyrrole, antifungal imidazole, antifungal alanine derivative and antifungal triazole,
   the herbicide is selected from the group consisting of cyclohexanedione, imidazolinone, sulfonylurea, triazinone, benzothiadiazinone, uracil, pyridazinone, urea, amide, diphenylether, triazolinone, isoxazolidinone, carbamate, chloracetamide, nitrile, thiocarbamate and triazine with the proviso that excluded as triazine are 6-chloro-N2,N4-diethyl-1,3,5-triazine-2,4-diamine; 1,3,5-triazine-2,4-diamine; and 6-chloro-N-(1,1-dimethylethyl)-N'-ethyl-2-tert-butylamino-4-chloro-6-ethylamino-s-triazine, and
   the sanitizing agent is selected from the group consisting of PHMB, chlorine, and bromine.

2. The composition of claim 1 wherein the cyclohexanedione is any of alloxydim, clethodim and sethoxydim.

3. The composition of claim 1 wherein the imidazolinone is asimazethapyr.

4. The compostion of claim 1 wherein the sulfonylurea is any of bensulfuron-methyl, chlorimuron-ethyl, chlorsulfuron, halosulfuron-methyl, methsulfuron-methyl and triflusulfruon-methyl.

5. The composition of claim 1 wherein the triazine is any of ametryn and prometryn.

6. The composition of claim 1 wherein the triazinone is any of hexazinone and metribuzine.

7. The composition of claim 1 wherein the benzothiadiazinone is bentazon.

8. The composition of claim 1 wherein the uracil is terbacil.

9. The composition of claim 1 wherein the pyridazinone is chloridazon.

10. The composition of claim 1 wherein the urea is chloroxuron.

11. The composition of claim 1 wherein the amide is propanil.

12. The composition of claim 1 wherein the diphenylether is acifluoren-sodium.

13. The composition of claim 1 wherein the triazolinone is carfentazone-ethyl.

14. The composition of claim 1 wherein the pyridazinone is norflurazon.

15. The composition of claim 1 wherein the isoxazolidinone is clomazone.

16. The composition of claim 1 wherein the carbamate is any of asulam, chlorpropham and propham.

17. The composition of claim 1 wherein the chloracetamide is any of alochlor and metalochlor and the sanitizing agent is PHMB.

18. The composition of claim 1 wherein the nitrile is dichlobenil.

19. A composition for controlling the growth of nuisance algae in a recirculating water system which composition comprises any of a herbicide having anti-algal activity in said water system, an agricultural fungicide having anti-algal activity in said water system or a combination thereof, and a sanitizing agent wherein,
   the fungicide is selected from the group consisting of methyl (E)-2-2-6-(2-cyanophenoxy)pyrimidin-4-yloxyphenyl-3-methoxyacrylate; 5,6-dihydro-2-methyl-N-phenyl-1,4-oxathiin-3carboxamide; cinnamaldehyde; S-ethyl cyclohexyl(ethyl)thiocarbamate; 2-cyano-N-[(ethylamino)carbonyl]-2-(methoxyamino) acetamide; 4-cyclopropyl-6-methyl-N-phenyl-2-pyrimidinamine; 5-butyl-2-ethylamino-6-methylpyrimidin-4-ol; (E,Z)-4-[3-(4-chlorophenyl)-3-(3,4-dimethoxyphenyl)acryloyl]morpholine; 1-dodecylguanidine acetate; 4-2,2-difluoro-1,3-bezodioxol-4-yl)-1H-pyrrole-3-carbonitrile; 1-[2-(2,4-dichlorophenyl)-2-(-2-propenyloxy)ethyl]-1H-imidazole; 3-(3,5-dichlorophenyl)-N-(1-methylethyl)-2,4-dioxo-1-imidazolidinecarboxamide; N-(2,6-dimethylphenyl)-N-(methoxyacetyl)-D-alaninemethyl ester; N-(2,6-dimethylphenyl)-N-(methoxyacetyl)-DL-alaninemethyl ester; propyl 3-(dimethylamino) propylcarbamate-hydrochloride; 1[[2-(2,4-dichlorophenyl)-4-propyl-1,3-dioxolan-2-yl]methyl]-1-H-1,2,4-triazole; H-1,2,4-triazole-1-ethanol-alpha-[2-(4-chlorophenyl)-ehtyl]-alpha-(1,1-dimethylethyl); 1-(4-chlorophenoxy)-3,3-dimethyl-1-(1H- 1,2,4-triazol-1-yl)-2-butanone; Beta-(4-chlorophenoxy)-alpha-(1,1-dimethylethyl)-1-1H-1,2,4-triazole-1-ethanol; 3-(3,5-dichlorophenyl)-5-methyl-5-vinyl-1,3-oxazolidine-2,4-dione,
   the herbicide is selected from the group consisting of alloxydim, clethodim, sethoxydim, asimazethapyr, bensulfruon-methyl, chlorimuron-ethyl, chlorsulfuron, halosulfuron-methyl, metsulfruon-methyl, triflusulfron-methyl, ametryn, prometryn, hexazinone, metribuzin, bentazon, terbacil, chloridazon, chloroxuron, propanil, acifluorfen-sodium, carfentazone-ehtyl, norflurazon, clomazone, asulam, chlorpropham, propham, alochlor, metalochlor and dichlobenil, and the sanitizing agent is selected from the group consisting of PHMB, chlorine, chlorine release agent, bromine, and ozone.

20. The composition of claim 19 wherein the herbicide is any of terbacil, alochlor, metalochlor and the sanitizing agent is PHMB.

21. The composition of claim 19 wherein the herbicide is free from triazine groups.

22. The composition of claim 19 wherein the herbicide is free from 4-fluoroalkyldiphenylether groups.

23. The composition of claim 19 wherein the antifungal triazole is H-1,2,4-triazole-1-ehtanol-alpha-[2-(4-chlorophenyl)-ethyl]-alpha-(1,1-dimethylethyl) and the sanitizing agent is PHMB 24. The composition of claim 19 wherein the fungicide contains a propyl or isopropyl group.

25. The composition of claim 19 wherein the herbicide is any of Hexazinone, Propanil, bensulfuronmethyl, and Terbacil and the agricultural fungicide is any of Dodine, cycolate, can carboxin.

26. A method of inhibiting the growth of microorganisms in a recirculating water system, which method comprises adding to the water system the components of the composition according to claim 1.

27. A method of inhibiting the growth of microorganisms in a recirculating water system, which method comprises adding to the water system the components of the composition according to claim 8.

28. A method of inhibiting the growth of microorganisms in a recirculating water system, which method comprises adding to the water system the components of the composition according to claim 17.

29. A method of inhibiting the growth of microorganisms in a recirculating water system, which method comprises adding to the water system the components of the composition according to claim 20.

30. A method of inhibiting the growth of microorganisms in a recirculating water system, which method comprises adding to the water system the components of the composition according to claim 23.

31. A kit for controlling the growth of nuisance algae in a recirculating water system, which kit comprises:
    (a) the components of the composition according to claim 1,
    (b) instructions for adding the components of (a) to the recirculating water system for controlling the growth of nuisance algae.

32. A kit for controlling the growth of nuisance algae in a recirculating water system, which kit comprises:
    (a) the components of the composition according to claim 8,
    (b) instructions for adding the components of (a) to the recirculating water system for controlling the growth of nuisance algae.

33. A kit for controlling the growth of nuisance algae in a recirculating water system, which kit comprises:
    (a) the components of the composition according to claim 17,
    (b) instructions for adding the components of (a) to the recirculating water system for controlling the growth of nuisance algae.

34. A kit for controlling the growth of nuisance algae in a recirculating water system, which kit comprises:
    (a) the components of the composition according to claim 20,
    (b) instructions for adding the components of (a) to the recirculating water system for controlling the growth of nuisance algae.

35. A kit for controlling the growth of nuisance algae in a recirculating water system, which kit comprises:
    (a) the components of the composition according to claim 23,
    (b) instructions for adding the compounds of (a) to the recirculating water system for controlling the growth of nuisance algae.

36. A recirculating water system comprising a composition for controlling the growth of nuisance algae in a recirculating water system which comprises,
    water,
    any of a herbicide having anti-algal activity in said water system, an agricultural fungicide having anti-algal activity in said water system or a comgination thereof, and a sanitizing agent wherein
    the fungicide is selected from the group consisting of antifungal methoxyacrylates, antifungal carboxamides, antifungal aldehydes, antifungal thiocarbamates, antifungal acetamides, antifungal pyrimidines, antifungal morpholines, antifungal guanidines, antifungal imidazoles, antifungal carbamate, antifungal oxazolidine, antifungal pyrrole, antifungal imidazaole, antifungal alanine derivative and antifungal triazole,
    the herbicide is selected from the group consisting of cyclohexanedione, imidazolinone, sulfonylurea, triazinone, benzothiadiazione, uracil, pyridazinone, urea, amide, diphenylether, triazolineone, isoxazolidinone, carbamate, chloracetamide, nitrile, thiocarbamate and triazine with the proviso that excluded as triazine are 6-chloro-N2,N4-diethyl1,3,5-triazine-2,4-diamine; 1,3,5-triazine-2,4-diamine, and 6-chloro-N-(1,1-dimethylethyl)-N'-ethyl-2-tert-butylamino-4-chloro-6-ethylamino-s-triazine,
    and the sanitizing agent is selected from the group consisting of PHMB, chlorine, bromine and ozone,
    a means for recirculating the water, and
    wherein the herbicide is present in an amount of about 0.1 to 30 ppm.

37. The system of claim 36 wherein the means for recirculating the water is a pump.

38. The recirculating system of claim 36 wherein the fungicide in present in an amount of about 0.1 to 24 ppm.

39. A recirculating water system comprising a composition for controlling the growth of nuisance algae in a recirculating water system which comprises,
    water,
    any of a herbicide having anti-algal activity in said water system, an agricurual fungicide having anti-alga activity in said water system or a combination thereof, and a sanitizing agent wherein,
    the fungicide is selected from the group consisting of methyl (E)-2-2-6-(2-cyanophenoxy)pyrimidin-4-yloxyphenyl-3-methoxyacrylate; 5,6-dihydro-2-methyl-N-phenyl-1-1,4-oxathiin-3-carboxamde; cinnamaldehyde; S-ethyl cyclohexyl(ethyl)thiocarbamate; 2-cyano-N-[(ethylamino)carbonyl]-2-(methoxyamino) acetamide; 4-cyclopropyl-6-methyl-N-phenyl-2-pyrimidinamine; 5-butyl-2-ethylamino-6-methylpyrimidin-4-ol; (E,Z)-4-[3-(4-chlorophenyl)-3-(3,4-dimethoxyphenyl)acryloyl]morpholine; 1-dodecylguanidine acetate; 4-(2,2-difluoro-1,3-bezodioxol-4-yl)-1H-pyrrole-3-carbonitrils; 1-[2-(2,4-dichlorophenyl)-2-(-2-propenyloxy)ethyl]-1H-imidazole; 3-(3,5-dichlorophenyl)-N-(1-methylethyl)-2,4-dioxo-1-imidazolidinecarboxamide; N-(2,6- dimethylphenyl)-N-(methoxyacetyl)-D-alaninemethyl ester; N-(2,6-dimethylphenyl)-N-(methoxyacetyl)-DL-alaninemethyl ester; propyl 3-(dimethylamino) propylcarbamate-hydrochloride; 1-[[2-(2,4-dichlorophenyl)-4-propyl-1,3-dioxolan-2-yl]methyl]-1H-1,2,4-triazole; H-1,2,4-triazole-1-ethanol-alpha-[2-(4-chlorophenyl)-ehtyl]-alpha-(1,1-dimethylethyl); 1-(4-chlorophenoxy)-3,3-dimethyl-1-(1H-1,2,4-triazol-1-yl)-2-butanone; Beta-(4-chlorophenoxy)-alpha-(1,1-simethylethyl)-1-1H-1,2,4-triazole-1-ehtanol; 3-(3,5-dichlorophenyl)-5-methyl-5-vinyl-1,3-oxazolidine-2,4-dione, the herbicide is selected from the group consisting of alloxydim, clethodim, sethoxydim, asimazethapry, bensulfuron-methyl, chlorimuron-ehtyl, chlorsulfuron, halosulfuron-methyl, metsulfuron-methyl, triflusulfuron-methyl, ametryn, prometryn, hexazinone, metribuzin, betazon, terbacil, chloridazon, chloroxuron, propanil. acifluoren-sodium, carfentazone-ehtyl, norflurazon, closmazone, asulam, chlorpropham, propham, alochlor, metalochlor and the sanitizing agent is dichlobenil, and the sanitizing agent is selected from the group consisting of PHMB, chlorine, and bromine, a means for recirculating the water, and wherein the herbicide is present in an amount of about 0.1 to 30 ppm.

40. The system of claim 39 wherein the means for recirculating the water is a pump.

41. The recirculating system of claim 39 wherein the fungicide in present in an amount of about 0.1 to 24 ppm.

42. The composition of claim 1 further comprising a carrier.

43. The composition of claim 19 further comprising a carrier.

44. The recirculating water system of claim 36 further comprising a carrier.

45. The recirculating water system of claim 39 further comprising a carrier.

* * * * *